(12) United States Patent
Yang et al.

(10) Patent No.: US 11,213,394 B2
(45) Date of Patent: Jan. 4, 2022

(54) GRAFT FOR SEGMENTAL BONE DEFECT REPAIR

(71) Applicant: The Board of Trustees of the Leland Stanford Junior University, Stanford, CA (US)

(72) Inventors: Yunzhi Yang, Stanford, CA (US); Arnaud Bruyas, Munich (DE); Michael J Gardner, 821 Stanford Avenue, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 16/970,368

(22) PCT Filed: Feb. 26, 2019

(86) PCT No.: PCT/US2019/019483
§ 371 (c)(1),
(2) Date: Aug. 16, 2020

(87) PCT Pub. No.: WO2019/165395
PCT Pub. Date: Aug. 29, 2019

(65) Prior Publication Data
US 2021/0085465 A1   Mar. 25, 2021

Related U.S. Application Data

(60) Provisional application No. 62/635,439, filed on Feb. 26, 2018.

(51) Int. Cl.
*A61F 2/28* (2006.01)
*A61F 2/30* (2006.01)

(52) U.S. Cl.
CPC .............. *A61F 2/28* (2013.01); *A61F 2/2846* (2013.01); *A61F 2/3094* (2013.01);
(Continued)

(58) Field of Classification Search
CPC ...................... A61F 2/2846; A61F 2002/2835
See application file for complete search history.

(56) References Cited

U.S. PATENT DOCUMENTS 3,720,959 A * 3/1973 Hahn .................... A61F 2/3099
                                                          623/17.17
9,433,707 B2    9/2016 Swords
(Continued)

OTHER PUBLICATIONS

Yu et al. A Revised Approach for Mandibular Reconstruction With the Vascularized Iliac Crest Flap Using Virtual Surgical Planning and Surgical Navigation. J Oral Maxillofac Surg 74:1285.e1-1285.e11, 2016.
(Continued)

*Primary Examiner* — Javier G Blanco
(74) *Attorney, Agent, or Firm* — Lumen Patent Firm

(57) ABSTRACT

A graft scaffold geometry is provided for use in the repair of segmental large bone defect. The scaffold geometry has a first (central) conduit with one or several hook-shaped chamber, which form a second conduit, integrated to the lateral side of the scaffold. The purpose of the hook-shaped chamber(s) is three-fold: 1) to facilitate the insertion and containment of biological augmentation constructs, such as growth factor-impregnated carrier devices; 2) stabilize the local surrounding soft tissue envelope to allow ingrowth of new blood vessels; and 3) to improve the manipulation of the composite bone free flap during implantation. Whether one or all of these mechanisms are active in a given situation, the overall result is that the hook chamber enables enhanced containment of graft-augmenting synthetic osteoinductive
(Continued)

constructs, prevents their displacement, and maintains their proximity to the scaffold, thus improving the chances of success of the graft.

8 Claims, 6 Drawing Sheets

(52) U.S. Cl.
CPC ............... *A61F 2002/2817* (2013.01); *A61F 2002/2835* (2013.01); *A61F 2002/30985* (2013.01)

(56) References Cited

U.S. PATENT DOCUMENTS

| | | | | |
|---|---|---|---|---|
| 2003/0083746 | A1* | 5/2003 | Kuslich | A61F 2/44 623/17.11 |
| 2007/0129804 | A1* | 6/2007 | Bentley | A61F 2/4455 623/17.11 |
| 2009/0088849 | A1* | 4/2009 | Armstrong | A61F 2/4455 623/17.16 |
| 2017/0354503 | A1* | 12/2017 | Larsen | A61F 2/30907 |
| 2018/0021140 | A1 | 1/2018 | Angelini | |
| 2018/0185547 | A1 | 7/2018 | Grayson | |
| 2018/0193149 | A1* | 7/2018 | An | A61C 19/06 |
| 2019/0274790 | A1* | 9/2019 | Karmon | A61F 2/2846 |

OTHER PUBLICATIONS

Chubb. Demonstration of cases and radiographs illustrating the technique employed and results obtained in the repair of fractured mandible by means of the free autogenous bone-graft. Proc R Soc Med 14:81, 1921.

* cited by examiner

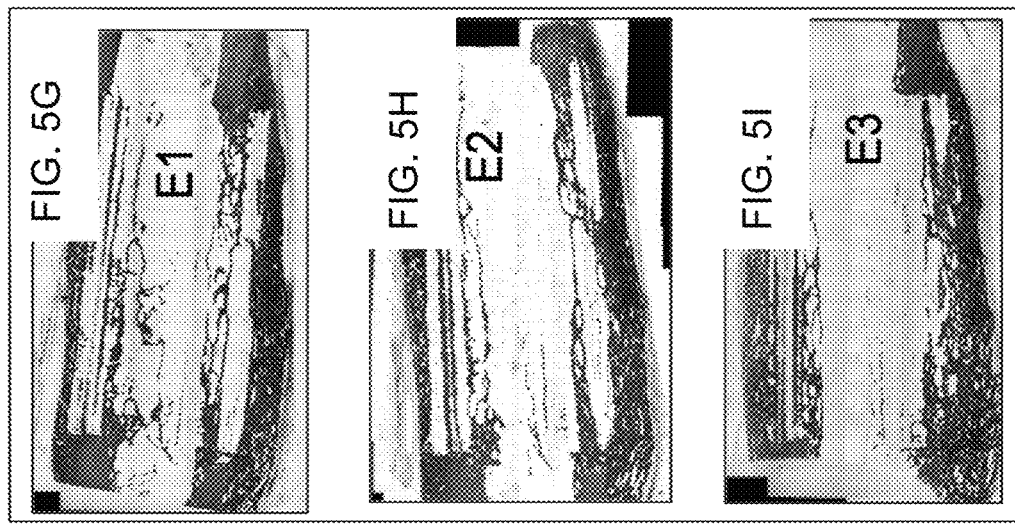
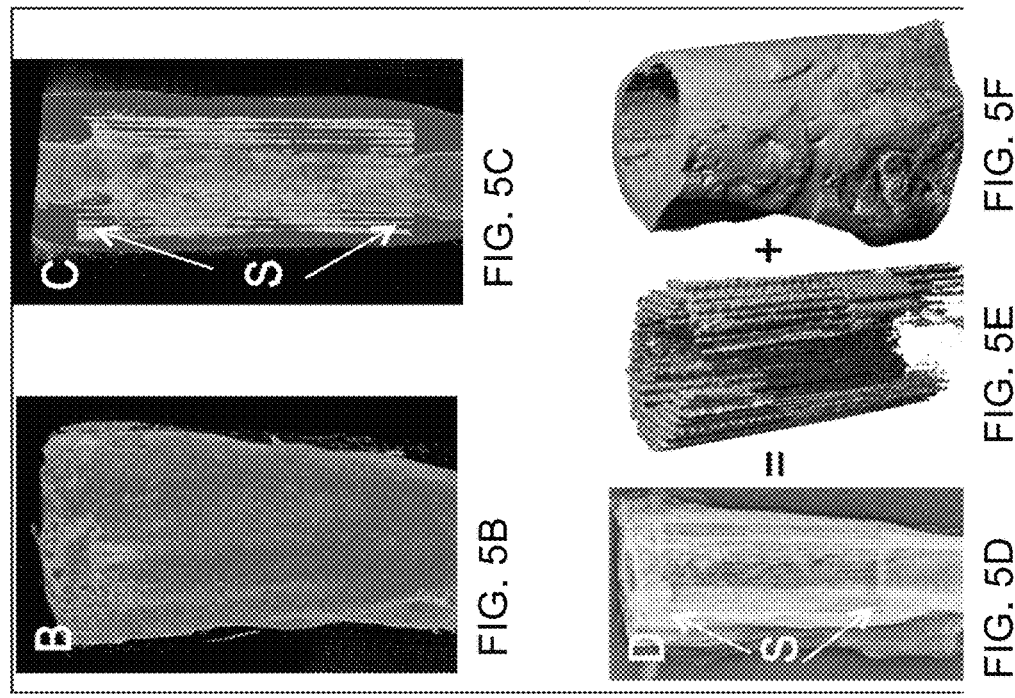
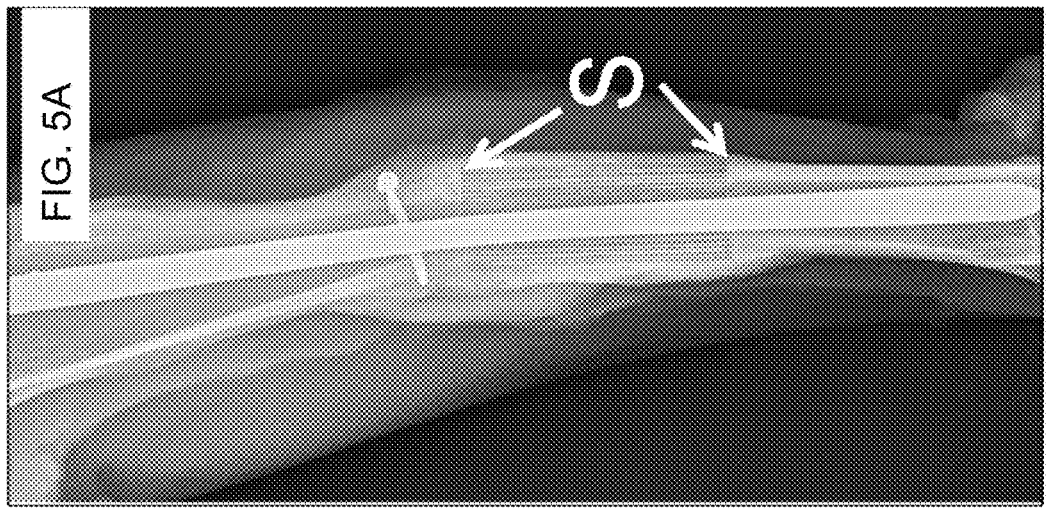

GRAFT FOR SEGMENTAL BONE DEFECT REPAIR

FIELD OF THE INVENTION

This invention relates to bone defect repair devices.

BACKGROUND OF THE INVENTION

Musculoskeletal diseases plague 30% of Americans and cost $950 billion per year, and each year more than a half million bone grafting surgeries are performed in the United States alone. Repair of large segmental bone defects still remains a significant clinical challenge. Despite much work to target this problem, vascularization remains a strategic barrier that prevents the translation of most bone tissue engineered constructs to clinical practice. The current technology will circumvent the harvesting of bone grafts, which causes skeletal morbidity in donor site and mismatch of anatomical shape. The present invention addresses solutions for large segmental long bone defects.

SUMMARY OF THE INVENTION

The present invention provides a personalized synthetic bioactive bone void filler or synthetic bioactive bone graft for large bone defect repair and regeneration. This bioactive synthetic bone graft will provide structural guidance and moderate mechanical support/protection for vascular invasion and bone regeneration, circumvent the perturbation and displacement of conventional use of synthetic osteoinductive adjuvants to avoid unpredictable growth factor release by mechanical support/protection, and circumvent the harvesting of bone grafts.

Specifically, the present invention provides a synthetic bioactive bone graft for bone defect repair and regeneration. The synthetic bioactive bone graft distinguishes a scaffold with a first conduit. The first conduit could be centrally situated to the scaffold and the scaffold could take any type of shape but in some cases a tubular or cylindrical scaffold would be preferred. The synthetic bioactive bone graft further distinguishes one or more hook-shaped chambers that are integrated with and expanding from a first lateral side of the scaffold. The one or more hook-shaped chambers shape or circumvent a second conduit that is capable to hold in place biological material, yet the one or more hook-shaped chambers leave a longitudinal opening close to a second lateral side of the scaffold. The opening is formed by the hook-shaped chamber(s) not fully closing to that other end of the scaffold as depicted in the drawings. In one embodiment, the first conduit and the second conduit are more or less parallel to each other.

The synthetic bioactive bone graft is made out of polycaprolactone and beta-tricalcium phosphate with a ratio of 80:20 or with a ratio ranging from 100:0 to 30:70. In other embodiments, the synthetic bioactive bone graft is made out of a polymer, polymer/ceramic composite, or a metal. The synthetic bioactive bone graft has a porous structure with a porosity between 30% to 90% to allow for vascular ingrowth and bone formation. In a preferred embodiment, the synthetic bioactive bone graft is a uniform or a single structure manufactured using 3D printing or molten material extrusion (MME), to allow for and control the porosity and shape of the synthetic bioactive bone graft.

Examples of the biological material are a growth factor, a recombinant human bone morphogenetic protein-2 (rhBMP-2) with a collagen sponge carrier, and/or a recombinant human plate-derived growth factor-BB (PDGF-BB) with a collagen sponge carrier.

BRIEF DESCRIPTION OF THE DRAWINGS

FIG. 3A shows 1 hook-shaped chamber, FIG. 3B shows 3 hook-shaped chambers, and FIG. 3C shows 3 hooks with the middle hook in a different direction from the top and bottom hook.

FIGS. 5A-I show according to an exemplary embodiment of the invention representative microCT and histology images of 3D printed scaffolds in the presence of rhBMP-2 to heal 5 cm tibia segmental bone defect in sheep at 6 months after implantation. (FIG. 5A) is a necropsy radiograph. (FIG. 5B) to (FIG. 5E) shows uCT 3D reconstruction. In FIG. 5B and FIG. 5C "dark grey area" indicates newly formed bone and "light strut line" indicates scaffold. (FIG. 5B) shows the overall volume and (FIG. 5C) shows the cross-section of 3D uCT reconstruction, and (FIG. 5D) show re-constructed mineral bone and scaffolds at 6 months after implantation. (FIG. 5E) and (FIG. 5F) show re-constructed mineral bone within a scaffold and callus surrounding scaffold at 6 months after implantation. (FIG. 5G-I) show histology images of 3D scaffold explants 6 months after implantation. S=scaffold.

DETAILED DESCRIPTION

Figure 1A:
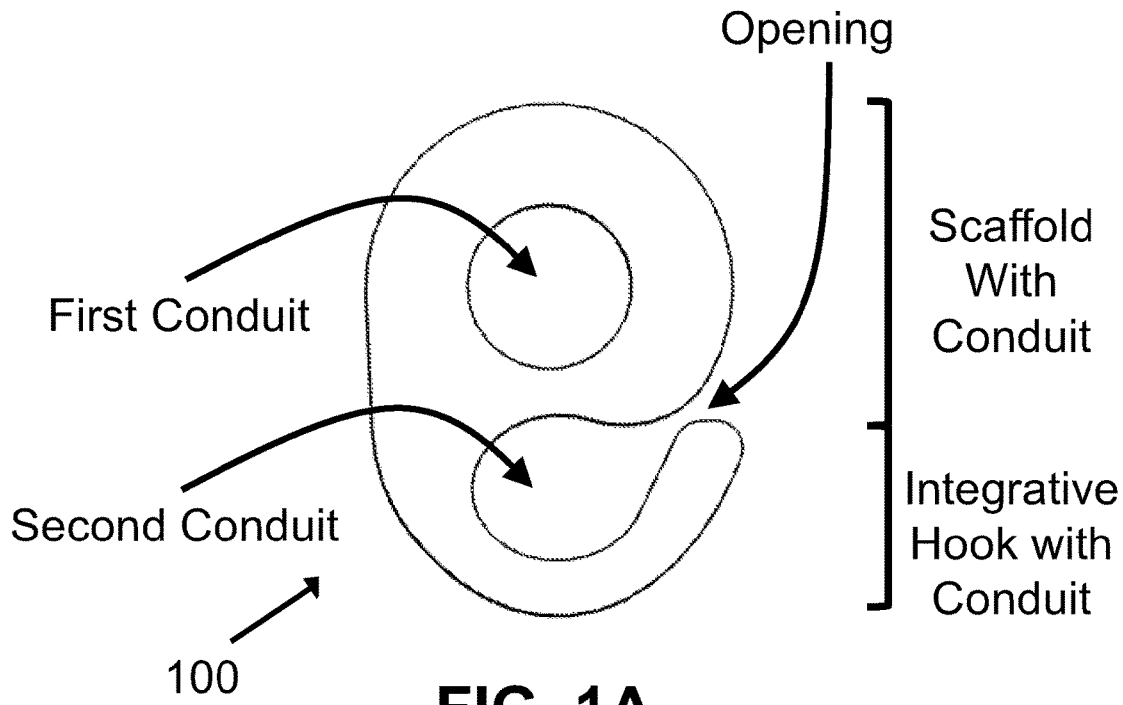
FIGS. 1A-B show according to an exemplary embodiment of the invention a device 100 (top view) and 110 (3D view) distinguishing a large bone defect scaffold with a first conduit and an integrated hook-shaped chamber with a second conduit. It is noted that the scaffold circumferences a first conduit, whereas the integrated hook-shaped chamber circumferences a second conduit yet leaving an opening close to the lateral section of the scaffold.
Figure 1B:
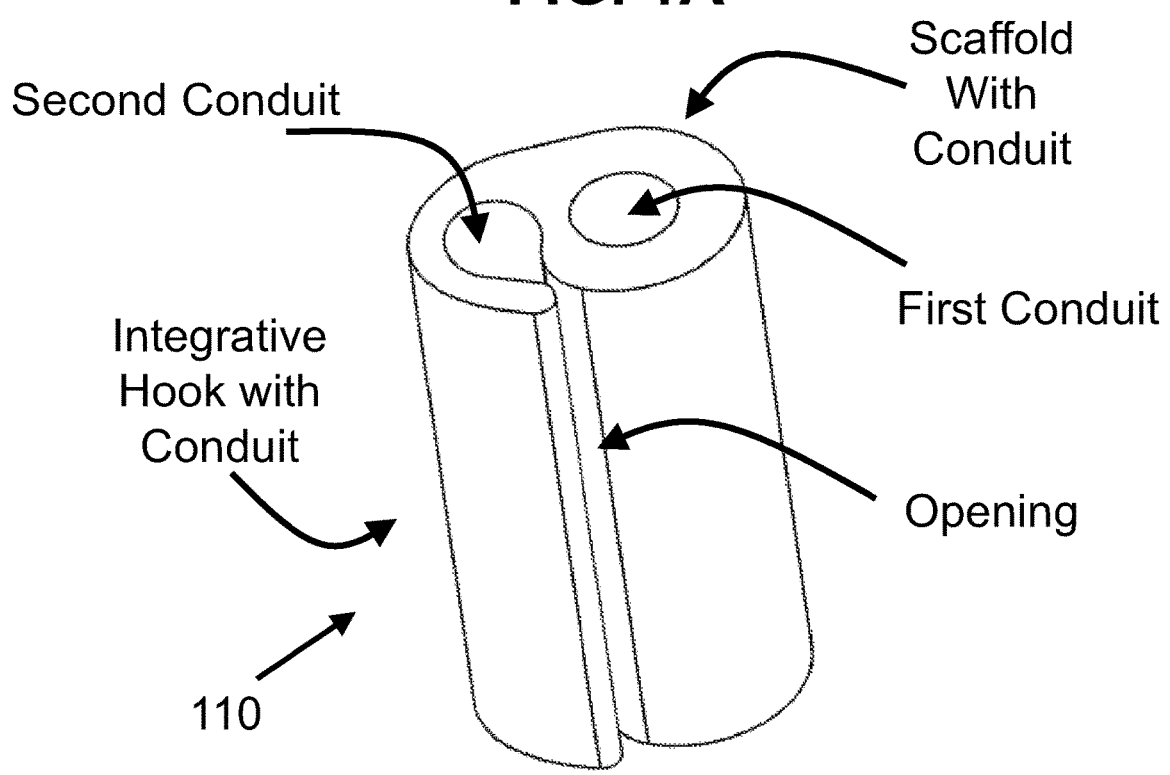

This invention pertains to a graft design for circumventing disadvantages of current clinical use of commercially available osteoinductive growth factors, and optimizing growth factor release for accelerated bone defect repair. The geometry of the device is distinguished by a scaffold section with a central conduit (first conduit), with either one or a series of hook-shaped chamber structures integrated and extending from a lateral side of the scaffold (FIGS. 1A-B, 2A-B and 3A-C). In one embodiment, the scaffold could be a tubular structure or a cylindrical structure. The purpose of the hook structures is to form a compartment or chamber, second conduit, to hold in place the biological augmentation device, such as growth factors (eg, recombinant human bone morphogenetic protein-2 (rhBMP-2) or platelet-derived growth factor BB (PDGF-BB) with carrier such as collagen sponge. In this case, the objective of the side hook is protection, so that during preparation and handling, the growth factor impregnated collagen sponge will not be accidently squeezed or displaced, avoiding inconsistent or erratic local release of growth factors. This stabilization of growth factor adjuvants will allow micro-vascular invasion from the surrounding tissues into the scaffold and osteogenesis within the scaffold. The hook structures are integrated with and extend in lateral direction from the scaffold and are shaped to circumvent conduit 2, yet leaving an opening at another lateral side of the scaffold as shown in FIGS. 1A-B.

The idea of opening was to make it relatively easy, flexible, and possible to insert for example a continuous blood bundle, which we have proven to be useful in insertion of other augmentation devices such as collagen as well. It is also flexible in placing augmentation devices with different dimensions, which could change in growth factor loading and release profiles. A large animal study by the inventors has proven that this side hook-shaped chamber design to be unprecedentedly, extremely efficient in promoting bone formation.

Figure 2A:
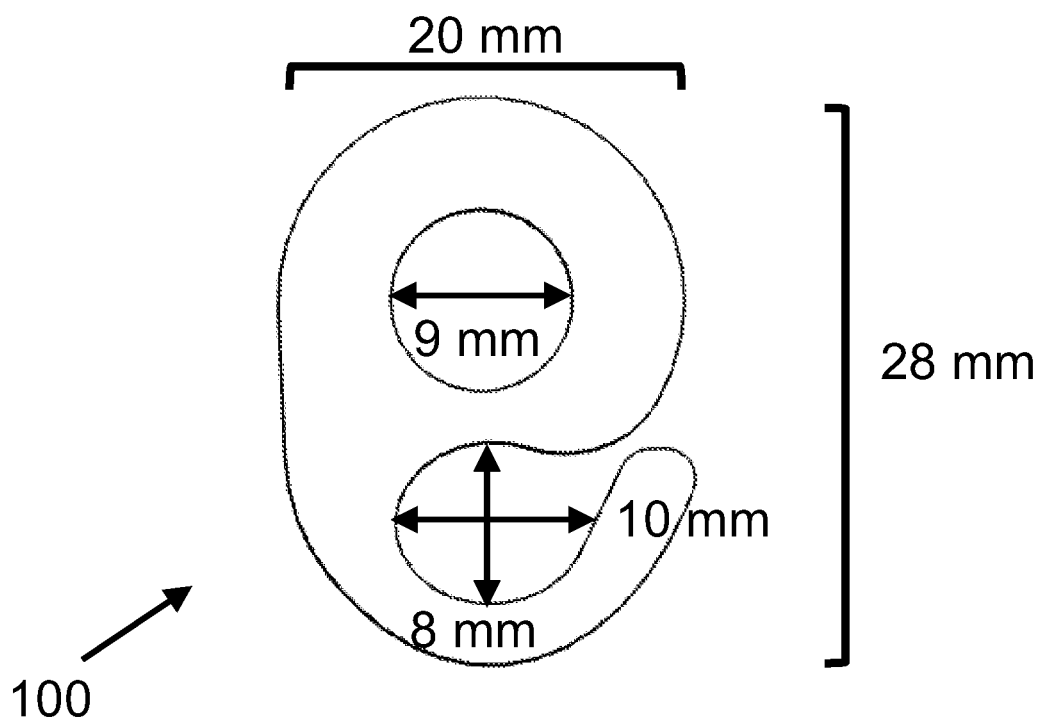
FIGS. 2A-B show according to an exemplary embodiment of the invention dimensions of the device 100 and 110.
Figure 2B:
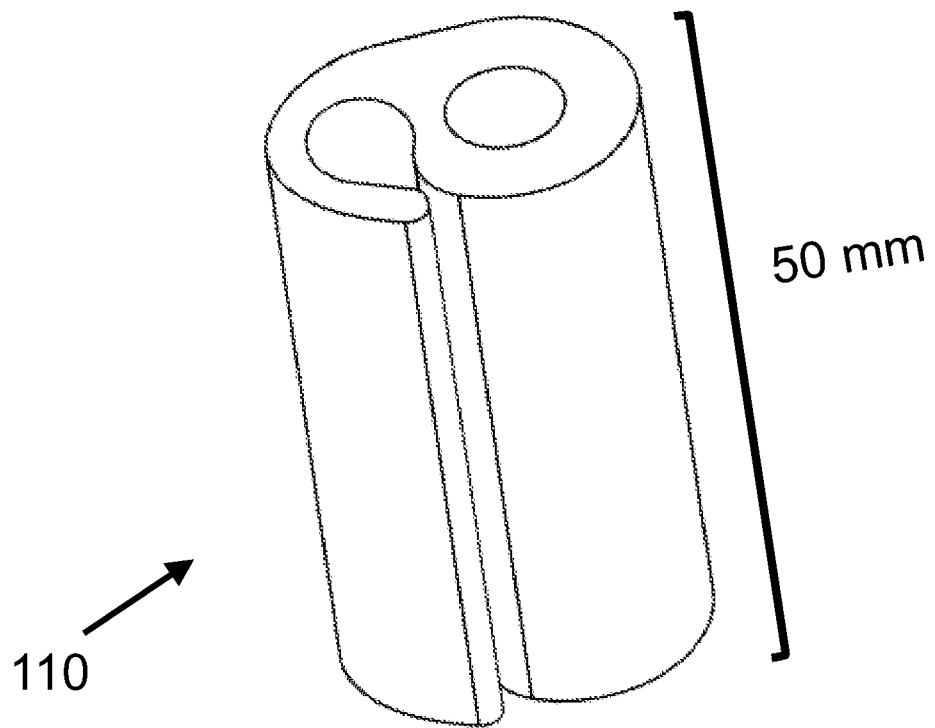
Figure 3A:
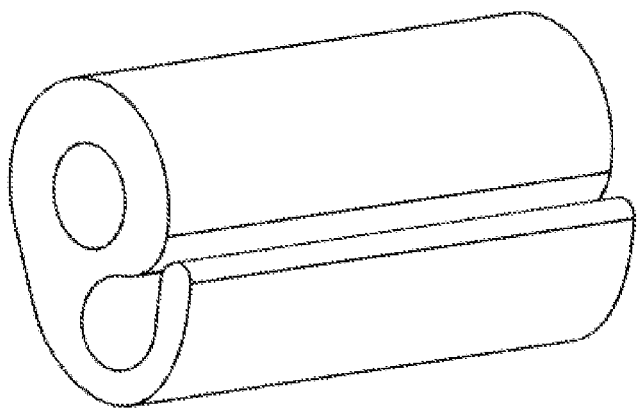
FIGS. 3A-C show according to an exemplary embodiment of the invention possible variation of the geometry of the integrated hook-shaped chamber.
Figure 3B:
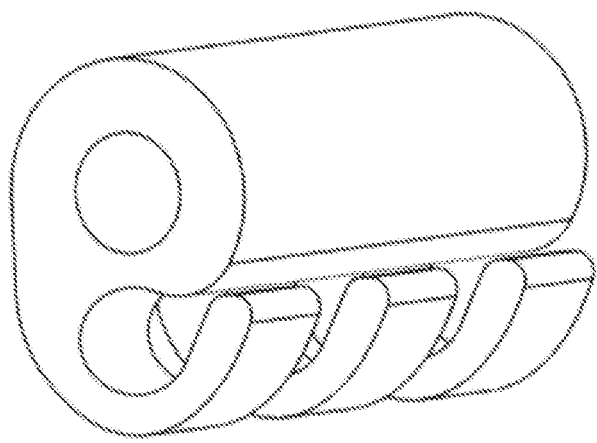
Figure 3C:
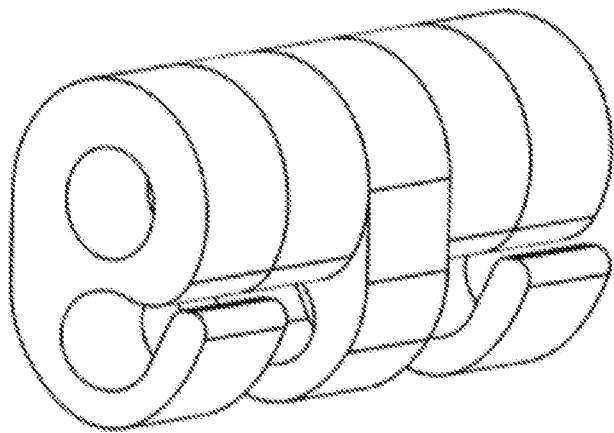
Figure 4:
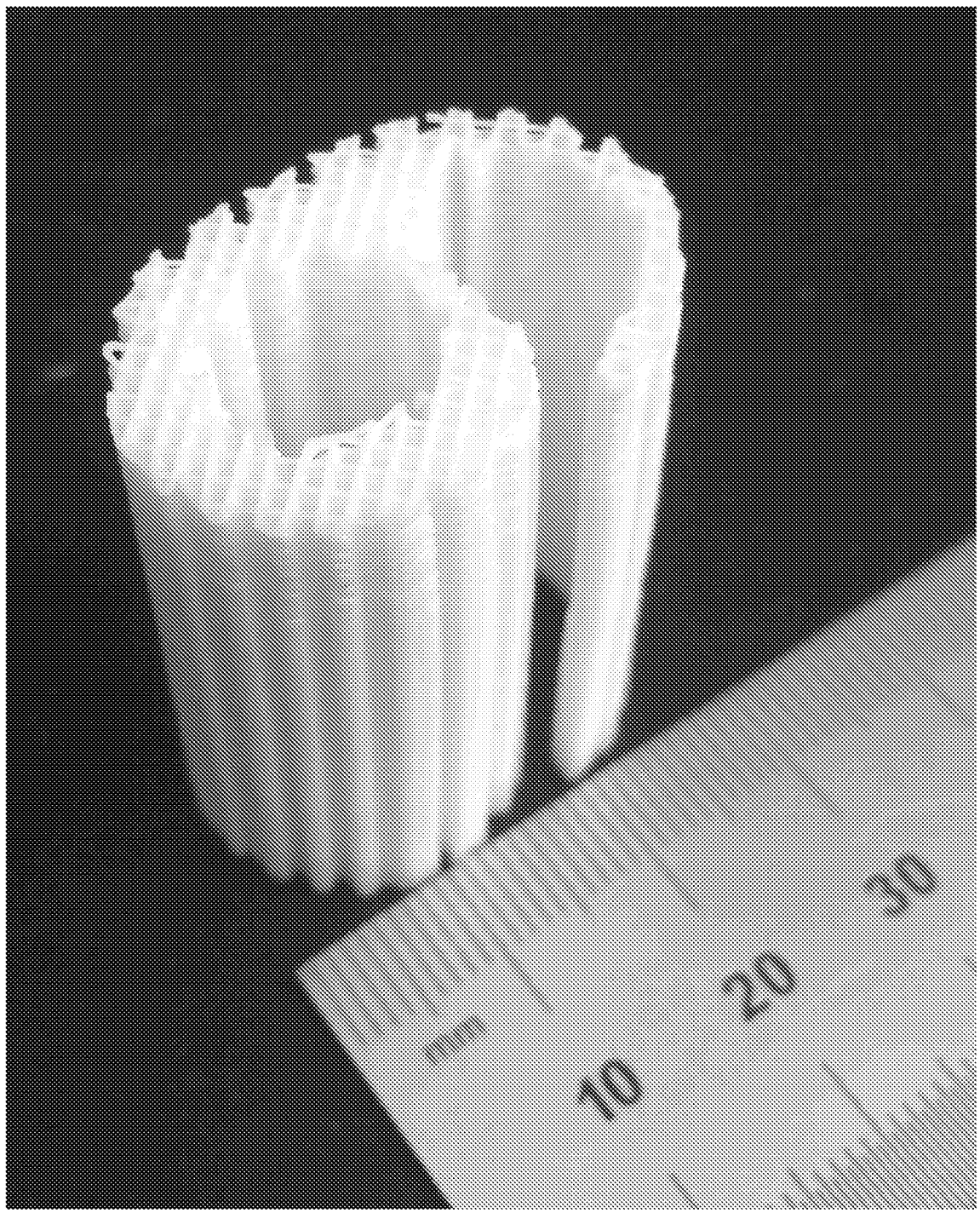
FIG. 4 shows according to an exemplary embodiment of the invention a scaffold after manufacturing. Interesting to note is the high porosity of the scaffolds, as well as the pattern of the struts.
Figure 6:
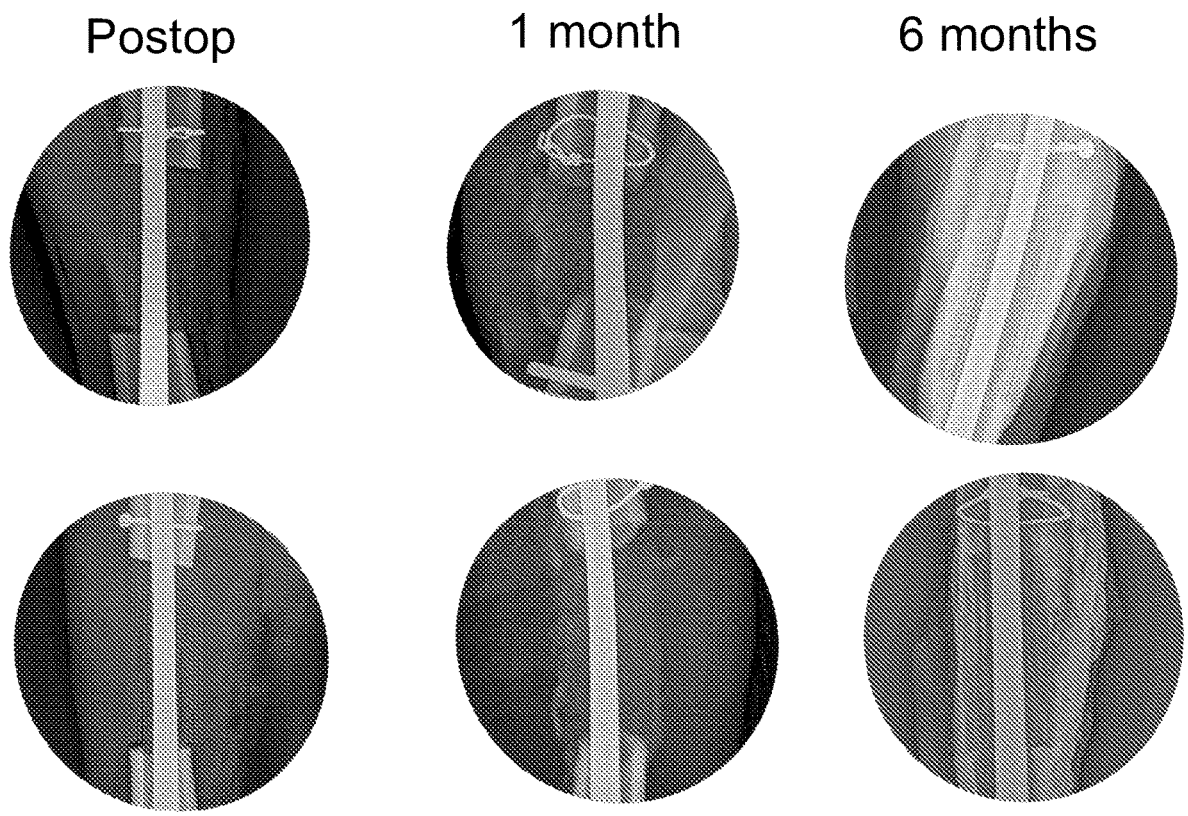
FIG. 6 shows according to an exemplary embodiment of the invention at 1 month post implantation, there is some mild bone formation along the caudal cortex on the proximal tibia and change in opacity within the scaffold suggestive of early bone formation. At 2 & 3 months (not shown), there is progressive increase in opacity (suggestive of ossification) at the caudal aspect of the defect and within the scaffold. Ossification within the defect and scaffold is progressively increasing. By 5-6 months (5 months no shown) it appears there is enough ossification for fracture stability.

The term "hook" defines any geometry integrated into the tubular scaffold that provides a conduit for biologicals such as bone infuse (rhBMP-2 impregnated collagen sponge) or vascular tissues onto the tubular structure. FIGS. 3A-C represent three examples of hook geometries. In FIG. 3A, the hook is integrated along the entire length of the tubular scaffold. In FIG. 3B, the hook is split in 3 different sections, allowing for easier insertion of the biologicals or tissue. In FIG. 3C, the hook is split in three sections, with the middle in the opposite direction, enabling better capture of the biologicals or tissue. The hook is compliant and has a low bending stiffness. It can therefore adapt to the size of the biological device without clamping impinging on them, but still maintaining their position relative to the scaffold. It is important to note that the scaffolds are highly porous (porosity between 30% to 90%) to allow for vascular ingrowth and bone formation. FIGS. 2A-B represents the overall shape of the scaffold, but the internal structure is made of a pattern of perpendicular struts and pores as shown in FIG. 4. The location and overall geometry of the hooks can be adjusted. They can also be adjusted using a cutting tool, such as a scalpel to allow for the following adjustments:

Slice the hook into several segments,
Create spacing between each hook,
Shorten the flexible segment of the hook,
If necessary, remove it completely, and/or
Or any other modifications susceptible to improve the surgical procedure.

The compliance of the hook(s) should allow some flexibility regarding the size of the tissue implanted inside.

In the example of placing a device such as a growth factor-impregnated collagen sponge into the hook-shaped chamber, the hook ensures that the device stays in place and is as close as possible to the tubular structure. It also increases the contact surface between vascular tissues and the graft, and therefore potentially improves the vascularization of the scaffold. Compared to suturing of the device to the scaffold, the use of a hook-shaped chamber prevents the clamping of the biological augment and increases its contact area.

3D Printing of Scaffold

After scanning of a skeletally mature sheep tibia, we selected a bone shaft segment of 5 cm and reconstructed the structure and geometry. Then, using a custom-built screw extruder, solid pellets of PCL/β-TCP were melted at 90° C. and extruded into a filament of constant diameter for FDM 3D printing. Average filament diameter for each group was measured and the values were used for each group respectively during the 3D printing process. Scaffolds were manufactured using a Lulzbot Mini (Aleph Objects Inc, USA) with a nozzle of 500 μm. The printing temperature was set to 160° C. so that each ratio could be printed smoothly. The layer thickness was set to 200 μm, each layer being constituted of parallel struts with an orientation of 90° relative to the previous layer. The printing speed was set to 5 mm/s, and was calibrated to deposit struts of width ranging from 350 μm to 400 μm. The specimens were cylinders of diameter 28 mm, and height 50 mm.

FIG. 4 represents a scaffold after manufacturing, made out of poly-caprolactone/beta-tricalcium phosphate (PCL:TCP, 80:20). In other variations, the material composition of the scaffold can be polymer, polymer/ceramic composite, or metal. In this case, it has been manufactured using, for example, but not limited to, 3D printing, specifically molten material extrusion (MME), which allows a high control of the pore geometry as well as the overall shape. In one example, polycaprolactone (PCL)/beta-tricalcium phosphate (β-TCP) scaffolds of approximately 5 cm long×2.0 cm in diameter were printed in a layer-by-layer fashion following a predefined trajectory. Each layer was composed of parallel struts of width 300-350 μm and thickness 200 μm, the overall geometry of the layer respecting the overall geometry of the scaffold. Struts of consecutive layers were oriented 90° with respect to each other, to form a porous scaffold with interconnected pores. Once manufactured, the scaffolds were surface treated by immersing them for 12 h in a sodium hydroxide solution (5M NaOH) at room temperature to improve hydrophilicity and create nanopores at the surface of the pores for better cell attachment.

Tibial Ostectomy, Placement of Scaffold into Defect and Tibial Nail Stabilization Using the Biomedtrix I-Loc IM Fixator The following is an example of a method of use or implantation of the scaffold in a sheep:

1. A sheep is placed in dorsal recumbency and a 2 cm skin incision is be made mid-way between the patellar tendon insertion and the medial collateral ligament.
2. The proximal tibia diaphysis is hand-reamed.
3. An 8 mm diameter×197 mm length tibial nail is inserted in normograde fashion from the proximal tibia through the 2 cm incision and driven only ⅓rd of the way down the tibial diaphysis.
4. A 10 cm skin incision is made down to the periosteum of the tibial mid-diaphysis on the medial side.
5. The overlaying soft tissues are elevated from the periosteum.
6. A mid-diaphyseal ostectomy of 5 cm is performed with an oscillating saw with constant lavage for tissue cooling.
7. The 5 cm scaffold is placed in the ostectomy and the tibial nail advanced across the ostectomy and into the distal tibial segment.
8. An Aiming Jig Arm is then connected to the proximal end of the nail to guide insertion of the 4 locking bolts through the tibial surface and the transverse cannulations within the interlocking nail: Two on each side of the ostectomy.
9. The surgical field is thoroughly lavaged in anticipation of wound closure.
10. Muscles and fascia surrounding the tibial defect directly over the scaffold are closed using a continuous pattern.
11. Subcutaneous tissue is closed using a continuous pattern.
12. Skin is closed using a Ford-Interlocking pattern.

What is claimed is:

1. A synthetic bioactive bone graft for bone defect repair and regeneration, comprising:
   (a) a tubular scaffold comprising a first end, a second end, and a first conduit extending along a longitudinal axis of the tubular scaffold;
   (b) one or more hook-shaped chambers integrated with and outwardly expanding from a first lateral side of the tubular scaffold, wherein the one or more hook-shaped chambers shape and circumvent a second conduit capable of holding in place biological material, wherein a free end of the one or more hook-shaped chambers is positioned immediately adjacent to a second lateral side of the tubular scaffold, and wherein a longitudinal opening is defined between the free end of the one or more hook-shaped chambers and the second lateral side of the tubular scaffold,
   wherein the synthetic bioactive bone graft has a porous structure with a porosity between 30% to 90% to allow for vascular ingrowth and bone formation,
   wherein the first conduit and the second conduit are substantially parallel to each other.

2. The synthetic bioactive bone graft as set forth in claim 1, wherein the synthetic bioactive bone graft is made out of poly-caprolactone (PCL) and beta-tricalcium phosphate (β-TCP) with a ratio of 80:20 (PCL-β-TCP) or with a ratio ranging from 100:0 to 30:70 (PCL-β-TCP).

3. The synthetic bioactive bone graft as set forth in claim 1, wherein the synthetic bioactive bone graft is made out of a polymer, polymer/ceramic composite, or a metal.

4. The synthetic bioactive bone graft as set forth in claim 1, wherein the synthetic bioactive bone graft is a uniform or a single structure manufactured using 3D printing or molten material extrusion (MME), to allow for and control the porosity and shape of the synthetic bioactive bone graft.

5. The synthetic bioactive bone graft as set forth in claim 1, wherein the biological material is a growth factor.

6. The synthetic bioactive bone graft as set forth in claim 1, wherein the biological material is a recombinant human bone morphogenetic protein-2 (rhBMP-2) with a collagen sponge carrier.

7. The synthetic bioactive bone graft as set forth in claim 1, wherein the biological material is a recombinant human plate-derived growth factor-BB (PDGF-BB) with a collagen sponge carrier.

8. The synthetic bioactive bone graft as set forth in claim 1, wherein the one or more hook-shaped chambers are monolithically-formed with the tubular scaffold.

* * * * *